US00PP13273P3

(12) United States Plant Patent
Noodelijk

(10) Patent No.: US PP13,273 P3
(45) Date of Patent: Nov. 26, 2002

(54) CHRYSANTHEMUM PLANT NAMED 'ADONIS'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/734,608

(22) Filed: Dec. 13, 2000

(65) Prior Publication Data

US 2002/0100097 P1 Jul. 25, 2002

(51) Int. Cl.[7] ..... A01H 5/00
(52) U.S. Cl. ..... Plt./298

(58) Field of Search ..... Plt./298

(56) References Cited

U.S. PATENT DOCUMENTS

PP3,833 P * 3/1976 Shoesmith ..... Plt./292

* cited by examiner

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A chrysanthemum plant named 'ADONIS' characterized by its small sized blooms with purple ray florets and prolific branching; natural season flower date September 1–6; blooming for a period of 6 weeks.

3 Drawing Sheets

BACKGROUND OF THE INVENTION

'ADONIS' is a product of a breeding and selection program for outdoor pot mums (garden mums) which had the objective of creating new chrysanthemum cultivars with a decorative type flower, a natural season flower date around September 1–6; blooming for a period of 6 weeks. The new plant of the present invention comprises a new and distinct cultivar of Chrysanthemum plant. 'ADONIS' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in September 1998. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
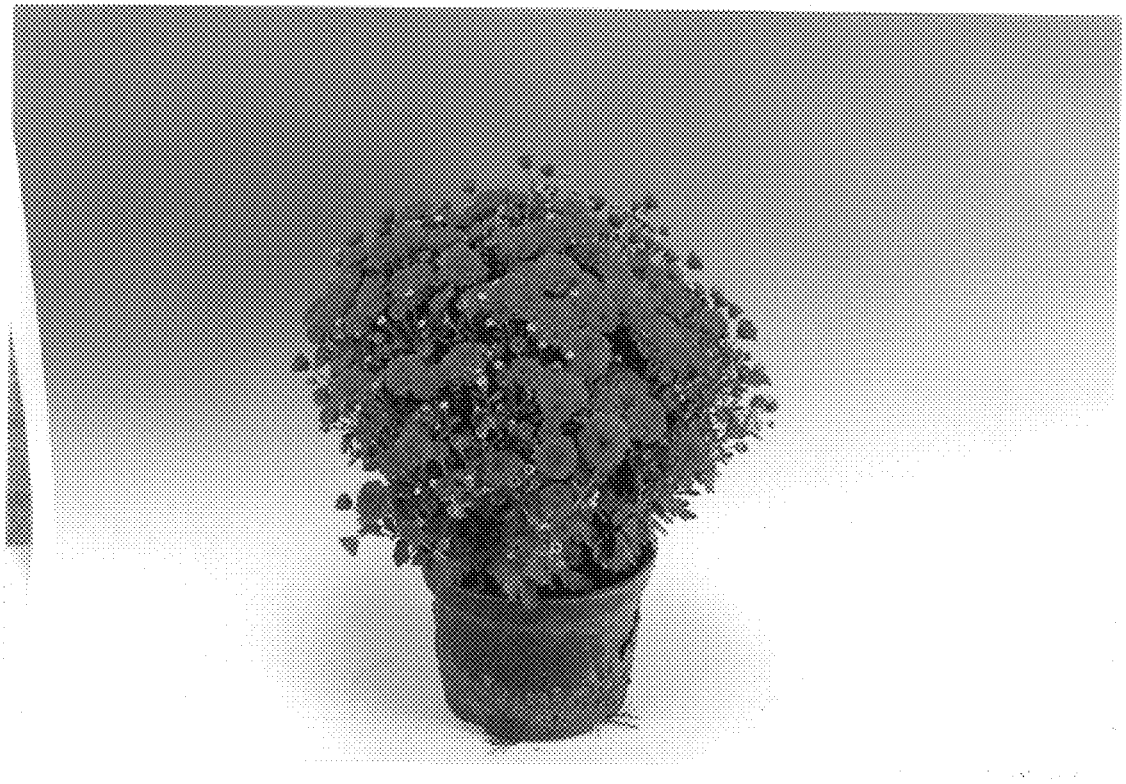
FIG. 1 shows a plant of the cultivar in full bloom.
Figure 2:
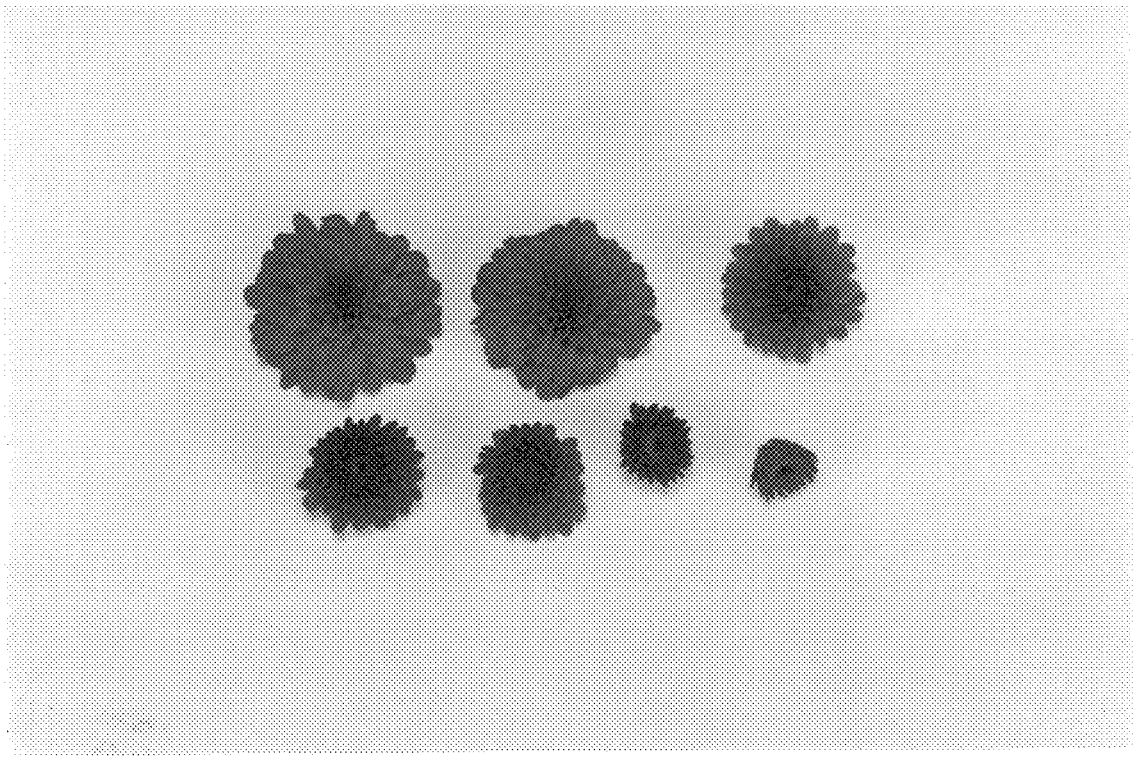
FIG. 2 shows the various stages of bloom of the new cultivar.
Figure 3:
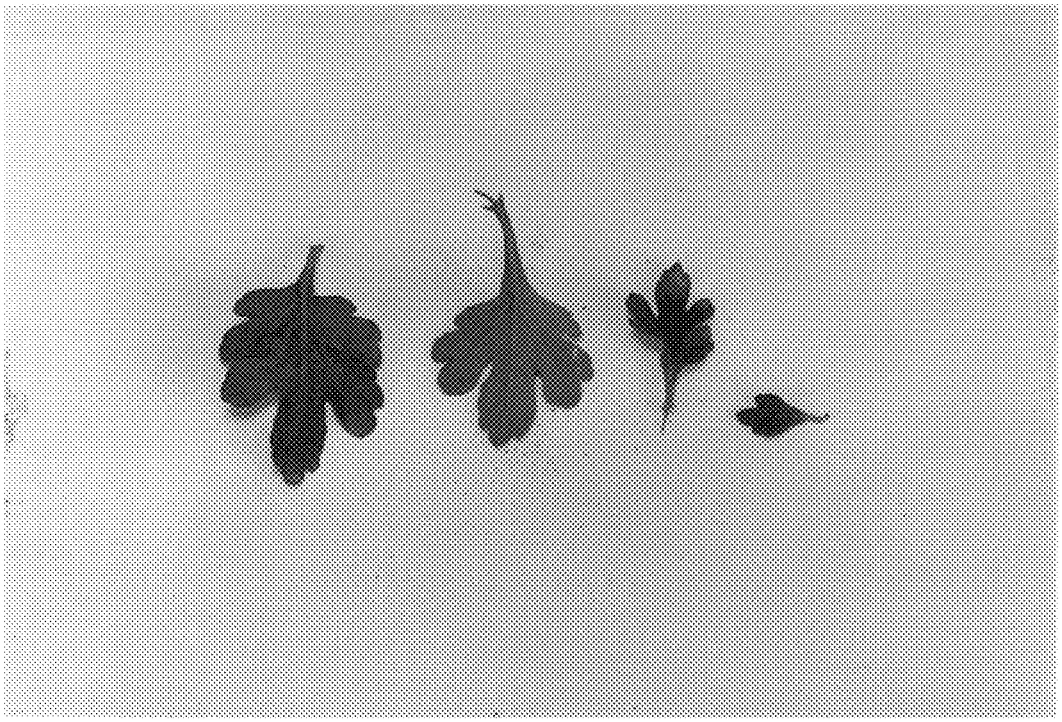
FIG. 3 shows the various stages of foliage and petiole of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 1999 and 2000. The natural blooming date of this crop was September 1–6 (week 35). The average height of the plants was 36–40 CM cms.

No growth retardants were used. No tests were done on disease or insects resistance or susceptibility. No tests were done on cold or drought resistance. This new variety produces small sized blooms with purple ray florets and a purple center blooming for a period of 6 weeks.

From the cultivars known to inventor the most similar existing cultivar in comparison to 'ADONIS' is 'DEBONAIR' (U.S. Plant Pat. No. 5,324). When 'DEBONAIR' and 'ADONIS' are being compared the following differences are noticed: The differences of 'DEBONAIR' and 'ADONIS' are (1) Natural blooming date. 'ADONIS' flowers earlier. (2) Branching. 'ADONIS' branches more prolific. (3) Plant shape. The plant shape of 'ADONIS' is semi-upright, the plant shape of 'DEBONAIR' is more spreading and rounded.

The following is a description of the plant and characteristics that distinguish 'ADONIS' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

TABLE 1

Botanical description of cultivar 'Adonis':

*Size.*—Small; cross-section 1.0 cm, height 0.7 cm.
*Outside color.*—Red-purple 64 A.
*Involucral bracts.*—2 rows, length 7 mm, width 3 mm.
*Involucral bracts among disc-florets.*—Not present.
*Involucral bracts color.*—Greyed-green 191 A.
*Type.*—Decorative.
*Height.*—Medium (3.0 cm).
*Size.*—Small.
*Fully expanded.*—3.5–4.0 cm.
*Number of blooms per branch.*—Approx. 5 blooms per branch.

*Performance on the plant.*—6 weeks.
*Seeds (if crossed).*—Produced in small quantities, ovate grey-brown 199 A, 1½ mm. in length.
*Fragrance.*—Typical chrysanthemum.

Color:
*Center of the flower (disc-florets).*—Immature red-purple 64 A. Mature red-purple 64 A.
*Color of upper surface of the ray-florets.*—Red-purple 70 A.
*Color of the lower surface of the ray-florets.*—Red-purple 70 B.
*Tonality from distance.*—A garden mum with purple flowers.
*Color of the upper surface of the flowers after aging of the plant.*—To red-purple 70B.

Ray florets:
*Texture.*—Upper and under side smooth.
*Number.*—170–200.
*Cross-section.*—Flat.
*Longitudinal axis of majority.*—Reflexing.
*Length of corolla tube.*—Medium, 0.8–1.0 cm.
*Ray-floret margin.*—Entire.
*Ray-floret length.*—1.8–2.0 cm.
*Ray-floret width.*—0.4–0.6 cm.
*Ratio length/width.*—Medium.
*Shape of tip.*—Rounded.
*Disc florets.*—Not present.

Reproductive organs:
*Stamen.*—Not present.
*Pollen.*—Not present.
*Styles.*—Thin.
*Style color.*—Yellow-green 144 A.
*Style length.*—4 mm.
*Stigmas color.*—Yellow-green 144 A.
*Stigma width.*—1 mm.
*Ovaries.*—Enclosed in calyx.

Plant:
*Shape.*—Semi-upright, corymbiform.
*Growth habit.*—Spreading.
*Growth rate.*—Rapid.
*Height.*—36–40 cm.
*Width.*—33–35 cm.
*Stem color.*—Greyed-green 191 A.
*Stem strength.*—Strong.
*Stem brittleness.*—Present.
*Stem anthocyanin coloration.*—Present, a slight layer of greyed-red 181 A mainly at the base of the stem.
*Length of lateral branch.*—From top to bottom 15–17 cm.
*Lateral branch color.*—Greyed-green 191 A.
*Lateral branch, attachment.*—Strong.
*Branching (average number of lateral branches).*—Prolific with 6–8 breaks after pinching.
*Peduncle length.*—4.5–5.0 cm.
*Peduncle color.*—Greyed-green 191 A.
*Natural season blooming date.*—September 1–6.

Foliage:
*Color of mature leaves.*—Upper side yellow-green 147 B. Under side yellow green 147 C.
*Color of immature leaves.*—Upper side green 138 A. Under side green 138 B.
*Size.*—Small; length 5.0 cm, width 4.0 cm.
*Quantity (number per lateral branch).*—9–12.
*Shape.*—Rounded.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Converging.
*Shape of base.*—Asymmetric.
*Apex.*—Mucronate.

TABLE 2

| Differences with the comparison varieties (when grown under the same conditions) | | |
|---|---|---|
| | 'ADONIS' | 'DEBONAIR' |
| Natural blooming date | 1–6 September | 20–23 September |
| Branching | Prolific | Less prolific |
| Plant Shape | Semi-upright (not so flat) | Spreading (more sounded/flat) |

I claim:

1. A new and distinct variety of chrysanthemum plant as described and illustrated.

* * * * *